(12) United States Patent
Jansen

(10) Patent No.: US 6,780,200 B2
(45) Date of Patent: Aug. 24, 2004

(54) PROSTHETIC MITRAL HEART VALVE

(75) Inventor: Josef Jansen, Köln (DE)

(73) Assignee: Adiam Life Science AG, Erkelenz (DE)

( * ) Notice: Subject to any disclaimer, the term of this patent is extended or adjusted under 35 U.S.C. 154(b) by 0 days.

(21) Appl. No.: 10/363,283
(22) PCT Filed: Aug. 25, 2001
(86) PCT No.: PCT/DE01/03333
§ 371 (c)(1), (2), (4) Date: Feb. 27, 2003
(87) PCT Pub. No.: WO02/24117
PCT Pub. Date: Mar. 28, 2002

(65) Prior Publication Data
US 2004/0102842 A1 May 27, 2004

(30) Foreign Application Priority Data
Sep. 19, 2000 (DE) .......................... 100 46 550

(51) Int. Cl.[7] ................................. A61F 2/24
(52) U.S. Cl. ....................... 623/2.17; 623/2.38; 623/2.3
(58) Field of Search ................................ 623/2.1, 2.11, 623/2.2, 2.21–2.29, 2.3, 2.31–2.38, 2.14, 2.17, 2.18, 900

(56) References Cited

U.S. PATENT DOCUMENTS

| 4,425,670 A | | 1/1984 | Figuera | |
|---|---|---|---|---|
| 4,605,407 A | * | 8/1986 | Black et al. | 623/2.17 |
| 4,759,759 A | * | 7/1988 | Walker et al. | 623/2.16 |
| 6,086,612 A | * | 7/2000 | Jansen | 623/2.17 |
| 6,113,631 A | * | 9/2000 | Jansen | 623/2.17 |
| 6,685,739 B2 | * | 2/2004 | DiMatteo et al. | 623/1.24 |

FOREIGN PATENT DOCUMENTS

| WO | WO 91/19465 | 12/1991 |
|---|---|---|
| WO | WO 97/49355 | 12/1997 |

* cited by examiner

Primary Examiner—Suzette J Jackson
(74) Attorney, Agent, or Firm—Herbert Dubno; Andrew Wilford

(57) ABSTRACT

The invention relates to a prosthetic mitral heart valve consisting of a support housing (10) comprising a base ring (15) supporting two posts which point essentially in the direction of the ring axis and which are connected by arc-shaped walls (13, 14), these walls being used to fix two flexible leaflets. The free ends of said posts form an inner support for the leaflet. The base ring, as seen from above, has a closed, noncircular shape with a common longitudinal axis but two different-sized semi lateral axes. The posts lie on the longitudinal axis and form the transitional point from one half of the shape to the other. The invention provides that in order to avoid undercuts which can contribute to turbulence, the plane in which the connection line (17) between the tips of the posts (18, 19), and the common longitudinal axis of the post base ring shape lie is tilted at an angle ($\alpha$) of 10° to 20°, preferably 15°, in relation to the plane that leads through the common longitudinal axis and lies vertically in relation to the surface (21) formed by the base ring; and the wall with the greater curvature supports the leaflet with the smaller surface (the mural leaflet), positioned at a greater angle to the surface formed by the base ring compared to the wall with the greater curvature.

8 Claims, 3 Drawing Sheets

PROSTHETIC MITRAL HEART VALVE

The invention relates to a prosthetic heart valve comprised of a support with a base ring that carries two posts extending axially of the ring, connected by arcuate walls serving for the mounting of two flexible cusps, and having outer edges forming an inside support for the respective cusps, the base ring seen from above having a closed noncircular shape with a major longitudinal axis and two unequal transverse minor subaxes, the posts extending from the major axis and forming transitions from the one to the other half.

Such a mitral heart valve is known from WO 97/49355. In order to avoid a potentially deleterious interference between the functions of the heart and of the valve, it is proposed in this publication that the wall with the smaller arc carry a cusp of smaller surface (mural) area than the wall with the larger arc. The two halves of the base ring thus form a stent body of kidney- or D-shape that is shaped like the natural mitral flap of the heart. In order to reduce the risk of interference and irritation of the heart lining by the support, it has further been suggested to incline the principal flow direction by 10° to 25°, preferably about 15°, from a perpendicular drawn from the mural cusps. The cusps should form a distinctly funnel-shaped passage with a smaller flow cross section than an aortic valve. Although this system and construction of the mitral heart valve is effective because of its physiologic flow from the auricle into the ventricles and its shortness compared to the hitherto known state-of-the-art systems with a circular or symmetrically elliptical support, turbulence is still present at the valve and occurs in locations in which the inner edge of the stent is undercut by the flow, that is in regions that have set-back edges and which form pockets trapping flow and that create undesired turbulence in the flow.

It is an object of the present invention to improve the described mitral heart valve by altering its shape such that such turbulence-creating undercuts are avoided.

This object is achieved by the prosthetic mitral valve according to claim 1 that is characterized in that a plane including a connecting line joining post tips and the major axis of the annulus of the post base ring is inclined vertically to the plane of the basis ring at an angle of 10° to 20°, preferably 15°, and the wall with the greater arc carries a cusp having a smaller surface (mural) area and inclined at a stronger angle to the base-ring plane than the wall with the larger arc. In this manner a support is produced whose flow direction defined by the angled walls is inclined at 10° to 20°, preferably 15°, to a perpendicular from the base-ring plane. In contrast to the D- or kidney-shape of WO 97,49355 the present invention has a 180° rotated D- or kidney-shape which produces a physiological flow from the auricle through the valve to the ventricle.

Further embodiments of the invention are describes in the dependent claims.

Thus preferably the flow direction defined by inner surfaces of the support is inclined at an angle from 70° to 80°, preferably 75°, to a base-ring plane. This means that the support inner surfaces which approach each other in the flow direction are inclined at 15° to a plane perpendicular from the base-ring plane and including the post-tip connecting line and planes parallel thereto.

According to a further embodiment of the invention the lengths of the minor subaxes form a ratio of from 1.5:1 to 2.5:1. In particular with a subaxis ratio of about 2:1 the shape is nearly that of a natural mitral valve. The major axis of the two different half ellipses of the support has a length between 10 mm and 45 mm. Preferably the posts are of the same thickness as the walls and are imbedded therein, that is the walls extend up and form posts at the ends of the posts which themselves are preferably rounded. In order not to stress the cusps too much in the attachment zone, according to a further feature of the invention the connecting lines of the cusps with the upper inner edges of the respective walls each lie in a plane.

The particular advantage of the mitral heart valve, in particular over such bioprostheses used to replace mitral heart valves where in practice 50% of the cases require blood thinners for the patient, is that the patient equipped with the mitral heart valve according to the invention can be spared these medications, since the new structure largely eliminates mechanical trauma to the blood.

An embodiment of the invention is shown in the drawing. Therein:

Figure 1:
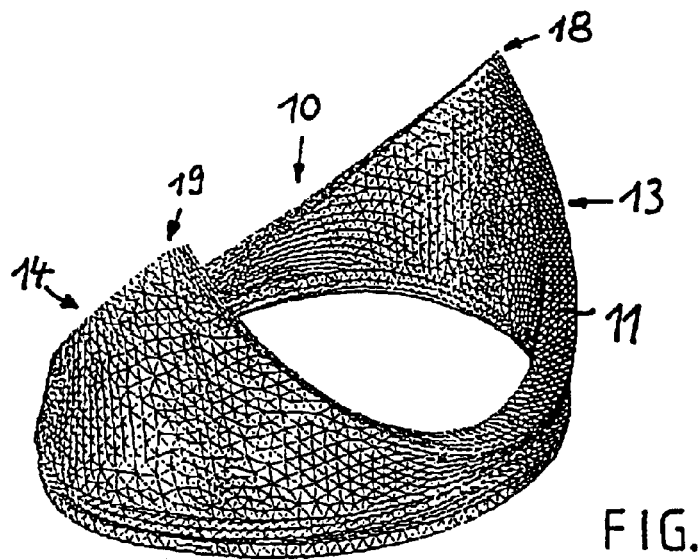
FIGS. 1 to 3 are perspective views of the mitral heart valve according to the invention seen from different angles.
Figure 2:
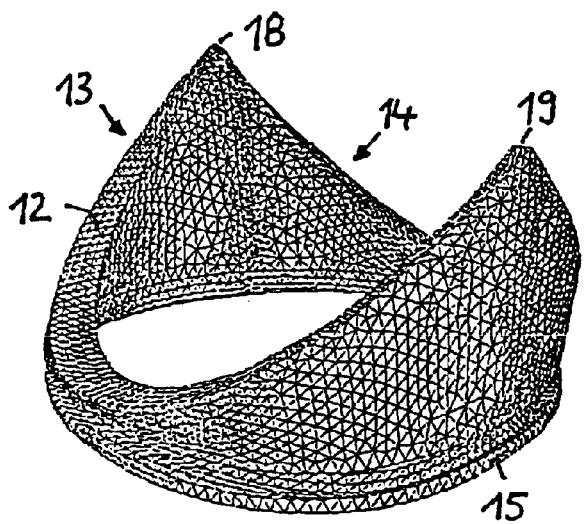
Figure 3:
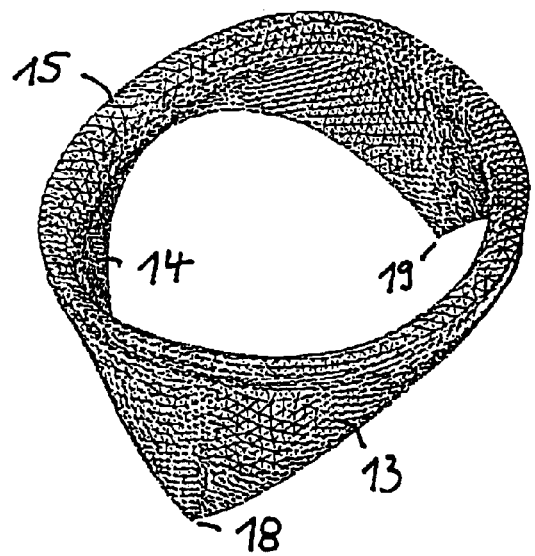
Figure 4:
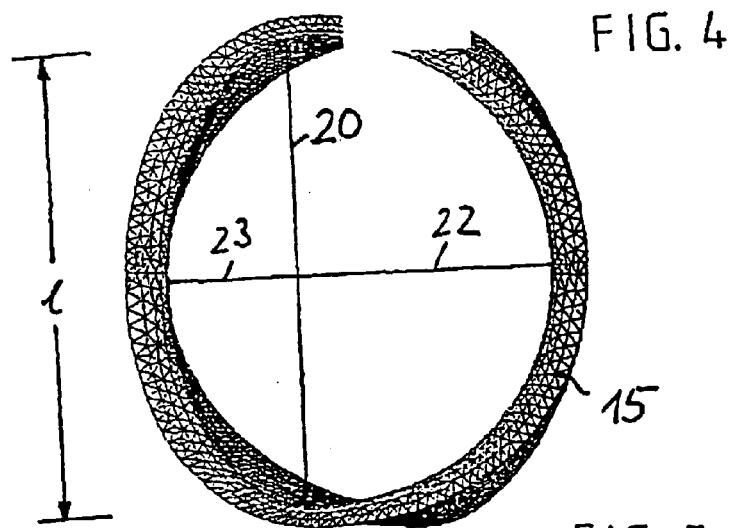
FIGS. 4 and 5 are view of the mitral heart valve from two directions (from above and from below)
Figure 5:
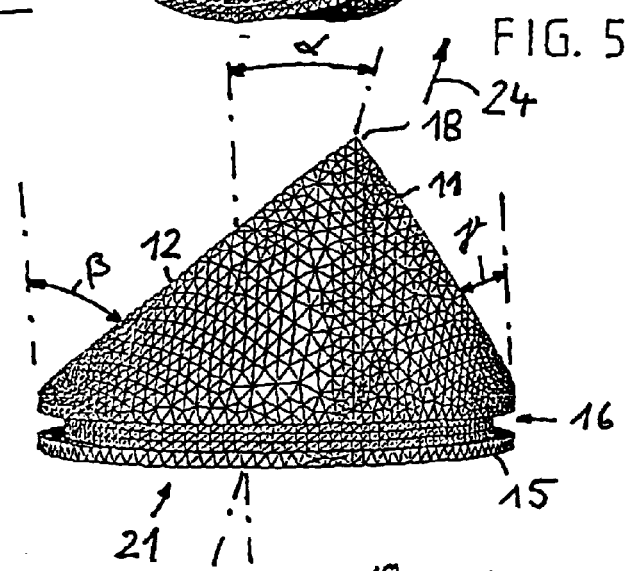

The prosthetic mitral heart valve is comprised of a support 10 with two (unillustrated) cusps of plastic, preferably polyurethane or a natural material, that are fixed to edges 11 and 12 of walls 13 and 14 in which the posts are imbedded. The support 10 is made of a thermoplastic, preferably polyurethane, that is made somewhat elastic, for example by injection molding. The support is unitarily formed with a base ring 15 whose inner edge is outwardly rounded as is known in the art. In order to best suture the base ring in place, it is formed with a groove 16. In contrast to the mitral heart valve shown in WO 97/49355, the walls 13 and 14 are not set perfectly perpendicular to the plane of the base ring, but at an angle α of about 15° (see in particular FIG. 6). Such an angle is characterized in that a plane including a connecting line 17 joining post tips 18 and 19 and a major axis 20 of the post-base ring shape extends at 15° to a plane extending through the major axis and perpendicular to a base-ring face 21. The wall 11 with the larger arc carries a cusp that is of smaller surface (mural) area and that extends at a steeper angle than the wall 12 with the larger arc. Unlike the shape from WO 97/49355, this produces in end view as shown in FIG. 4 a mirror-reversed D-shape where a longer minor subaxis 22 seen in end view is to the right of the base ring and a shorter minor subaxis 23 is on the left side. The geometric "tipping" of the plane running through the lines 17 and 20 relative to the perpendicular one produces a flow direction 24 through the support that is inclined at angle of 75° to the base-ring plane. The relationship of the lengths of the minor subaxes 22 and 23 is in a relationship of 2.5:1 to 1.5:1. The major axis 20 has a length between 10 mm and 45 mm. In this embodiment the posts are of the same thickness as the walls 11 and 12, these posts 18 and 19 terminating in sharp points. The connecting line of the cusps with the upper inner edges 11 and 12 of the walls 13 and 14 are each in a plane. As visible in FIG. 5, the less angled aortal cusp is set about at an angle β=40° and the more angled mural cusp about at an angle γ=55°.

Figure 6:
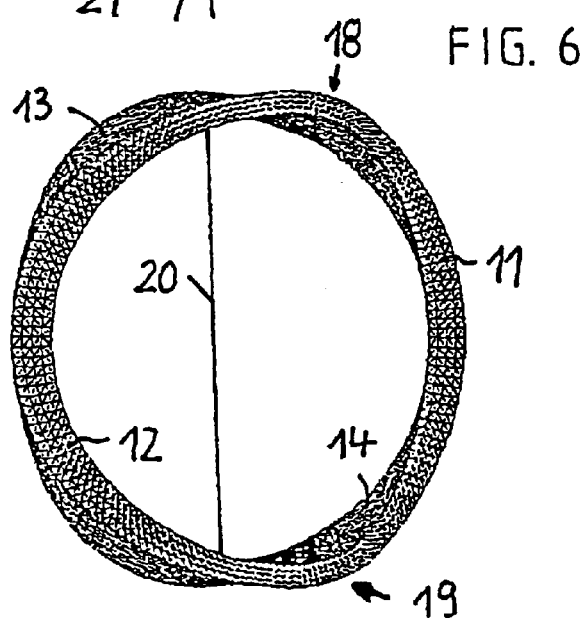
FIGS. 6 and 7 are two side views of the mitral heart valve.
Figure 7:
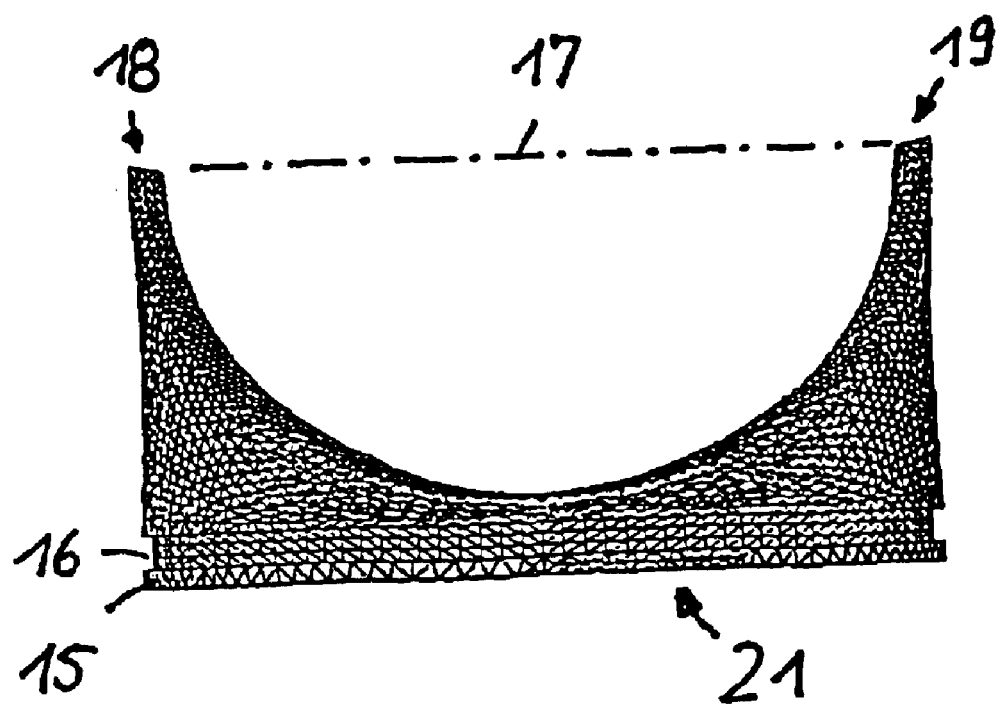

The end view against the flow direction of FIG. 6 shows that the projection on the cusp attachment edges 11 and 12 also has a kidney- or D-shape which is once again mirror symmetrical to the base-ring shape, that is the shorter minor subaxis is on the right, so that in the downstream region the shape of the cusp surfaces is that same as the shape described in WO 97/49355.

What is claimed is:

1. A prosthetic heart valve comprising:

a support formed with a base ring defining a ring plane, of noncircular shape, and having a relatively long major axis and a relatively short minor axis perpendicular to the major axis and defined by short and long minor subaxes meeting at the major axis;

a pair of arcuate walls projecting transversely of the plane from the base ring generally to respective sides of the major axis, meeting at points directed away from the base ring, and having arcuate edges extending between the points, one of the walls forming a larger arc than the other of the walls, the walls being shaped such that a point plane including a line connecting the points and the major axis forms with a plane including the major axis and perpendicular to the ring plane an angle of between 10° and 20°; and respective flexible valve cusps attached to the edges, the valve cusp attached to the edge of the smaller-arc wall being of smaller surface area than and inclined at a more obtuse angle to the ring plane than the valve cusp attached to the edge of the larger-arc wall.

2. The prosthetic heart valve defined in claim 1 wherein the support defines a flow direction extending at an angle of between 70° and 80° to the ring plane.

3. The prosthetic heart valve defined in claim 1 wherein the edge of the smaller-arc wall lies in a plane extending at between 55° and 70° to the ring plane and the edge of larger-arc wall at an angle of between 25° and 45° to the ring plane.

4. The prosthetic heart valve defined in claim 1 wherein the long minor subaxis has a length forming with a length of the short minor subaxis a ratio of between 1.5:1 and 2.5:1.

5. The prosthetic heart valve defined in claim 1 wherein the major axis has a length between 10 mm and 25 mm.

6. The prosthetic heart valve defined in claim 1 wherein the walls include imbedded posts at the corners.

7. The prosthetic heart valve defined in claim 1 wherein the posts extend to the points.

8. The prosthetic heart valve defined in claim 1 wherein the cusps are connected to the respective edges along respective lines lying in respective planes.

* * * * *